United States Patent [19]
DiFilippo

[11] Patent Number: 5,998,792
[45] Date of Patent: Dec. 7, 1999

[54] POSITRON EMISSION TOMOGRAPHY WITH VARIABLE DETECTOR GEOMETRY

[75] Inventor: Frank P. DiFilippo, University Heights, Ohio

[73] Assignee: Picker International, Inc., Cleveland, Ohio

[21] Appl. No.: 09/017,505

[22] Filed: Feb. 2, 1998

[51] Int. Cl.⁶ .................................................. G01T 1/166
[52] U.S. Cl. .............................. 250/363.05; 250/363.03; 250/363.08
[58] Field of Search ........................ 250/363.02, 363.03, 250/363.04, 363.05, 363.08

[56] References Cited

U.S. PATENT DOCUMENTS

| | | |
|---|---|---|
| 4,204,123 | 5/1980 | Stoddart . |
| 4,309,611 | 1/1982 | Tanaka et al. . |
| 4,352,018 | 9/1982 | Tanaka et al. . |
| 4,473,749 | 9/1984 | Derenzo et al. . |
| 4,642,464 | 2/1987 | Mullani . |
| 5,331,553 | 7/1994 | Muehllehner et al. . |
| 5,349,190 | 9/1994 | Hines et al. ....................... 250/363.05 |
| 5,451,789 | 9/1995 | Wong et al. . |
| 5,532,489 | 7/1996 | Yamashita et al. . |
| 5,591,977 | 1/1997 | Green et al. . |
| 5,602,395 | 2/1997 | Nellemann et al. . |
| 5,608,221 | 3/1997 | Bertelsen, et al. . |
| 5,777,331 | 7/1998 | Muehllehner ...................... 250/363.03 |

OTHER PUBLICATIONS

United States Statutory Invention Registration; Reg. No. H12 Published Jan. 7, 1986; Bennett, et al.; Nuclear Medicine Imaging System.

Primary Examiner—Constantine Hannaher
Assistant Examiner—Albert Gagliardi
Attorney, Agent, or Firm—Timothy B. Gurin; John J. Fry; Eugene E. Clair

[57] ABSTRACT

An imaging apparatus includes a plurality of detector assemblies disposed for rotation about an imaging region. The detector assemblies may be adjusted between at least two relative angular orientations about the imaging region. The relative angular orientations are selected based on the size of an object within the imaging region. The center of the transverse fields of view of the detectors may be offset from the axis of rotation. Gamma radiation generated by positron annihilation events is detected and used to generate tomographic images.

12 Claims, 5 Drawing Sheets of radiation detectors. One class of PET

POSITRON EMISSION TOMOGRAPHY WITH VARIABLE DETECTOR GEOMETRY

BACKGROUND

The present invention relates to the field of diagnostic imaging, and specifically to the field of positron coincidence imaging.

In nuclear imaging, a radiopharmaceutical such as $^{99m}$Tc or $^{201}$Tl is introduced into the body of a patient. As the radiopharmaceutical decays, gamma rays are generated. These gamma rays are detected and used to construct a clinically useful image.

Positron emission tomography (PET) is a branch of nuclear medicine in which a positron-emitting radiopharmaceutical such as $^{18}$F-Fluorodeoxyglucose (FDG) is introduced into the body of a patient. Each emitted positron reacts with an electron in what is known as an annihilation event, thereby generating a pair of 511 keV gamma rays. The gamma rays are emitted in directions approximately 180° apart, i.e. in opposite directions.

A pair of detectors registers the position and energy of the respective gamma rays, thereby providing information as to the position of the annihilation event and hence the positron source. Because the gamma rays travel in opposite directions, the positron annihilation is said to have occurred along a line of coincidence connecting the detected gamma rays. A number of such events are collected and used to reconstruct a clinically useful image.

Various detector systems have been used in PET imaging. One class of PET systems can be termed non-rotating systems. The most common non-rotating systems have one or more rings of detector elements disposed in a circle about the patient. Other non-rotating systems include cylindrical shell detector systems and hexagonal multi-plate systems. In each of these systems, the detector surrounds or nearly completely surrounds the object to be scanned. Since coincidence events at substantially all transverse angles within a slice can be detected, system sensitivity is does not vary much between locations in a transverse slice.

Another class of PET systems can be termed rotating systems. Partial ring systems and dual or triple head gamma camera systems with coincidence detection capabilities fall into this category. One type of partial ring system includes two arcs of radiation sensitive detectors disposed on a generally circular rotating gantry. The arcs of radiation detectors are fixed with respect to each other so that their centers are generally diametrically opposed, with a slight angular offset. Rotating systems have partial transverse angle coverage such that it is necessary to rotate the detectors about the patient (or vice versa) in order to sample the transverse angles needed to reconstruct fully tomographic images. The sensitivity of these systems thus varies across the detector field of view. This variation in sensitivity is taken into account during processing of the coincidence data.

Nonetheless, the variations in sensitivity which are characteristic of rotating systems are undesirable for a number of reasons. Larger objects are not well covered because the transverse extent of the detector field of view is limited. Count statistics also vary significantly across the field of view, causing a variation in image quality. Also, with relatively fewer true counts available at various locations in the field of view, correction of random and scatter counts is complicated. The present invention addresses these problems, and others.

SUMMARY

According to a first aspect, present invention provides an imaging method for use with an apparatus which includes a plurality of detector assemblies. Each detector assembly includes a radiation sensitive face which faces an imaging region, generates an output signal indicative of the axial and transverse coordinates at which radiation has been detected, and has a field of view in the transverse direction. The method includes the steps of detecting gamma radiation characteristic of a plurality of positron annihilation events, rotating the detectors about an axis of rotation, the centers of the transverse fields of view of the detectors being offset from the axis of rotation, repeating the step of detecting, and generating an image indicative of the positron annihilation events.

According to a more limited aspect, the apparatus includes two detector assemblies disposed 180 degrees opposite each other and the centers of the transverse fields of view coincide.

According to another more limited aspect, each detector assembly includes a plurality of radiation sensitive elements disposed in a two dimensional array. According to a yet more limited aspect, the radiation sensitive elements are photomultiplier tubes.

According to still another more limited aspect, the method also includes the step of moving the detectors in a tangential direction until the offset between the centers of the transverse fields of view of the detectors and the axis of rotation reaches a desired value.

According to yet another more limited aspect of the present invention, the apparatus includes three detector assemblies. The method includes the steps of determining an orbit radius required to image an object located in the imaging region, determining a desired relative angular orientation depending on the required orbit radius, and positioning the detector assemblies in the desired relative angular orientation.

According to another aspect of the present invention, an imaging method utilizes an apparatus which includes a plurality of detector assemblies disposed about an imaging region. The method includes the steps of determining a size of an object within the examination region, adjusting the relative angular orientations of the detector assemblies depending on the size of the object, detecting gamma radiation indicative of a plurality of positron annihilation events, and generating an image indicative of the annihilation events.

According to a more limited aspect of the invention, the image is a tomographic image and the method includes the step of rotating the detectors about the examination region.

According to another more limited aspect, the apparatus includes three detector assemblies. The method includes the step of positioning the detector assemblies in a first relative angular orientation if the size of the object is less than a threshold value and in a second relative angular orientation if the size of the object is greater than the threshold value. According to a still more limited aspect, the detector assemblies are placed at equal angular intervals about the imaging region if the size of the object is less than a threshold value. According to a another still more limited aspect, the detector assemblies are placed at 90 degree angular intervals if the size of the object is greater than the threshold value.

According to another aspect of the present invention, a method of imaging uses an apparatus which includes a plurality of radiation detectors disposed about an examination region. The method includes the steps of determining an orbit radius to be used in an imaging procedure, adjusting the relative angular orientation of the radiation detectors depending on the orbit radius, detecting gamma radiation characteristic of a plurality of positron annihilation events, rotating the radiation detectors with respect to the imaging region, repeating the steps of detecting and rotating, and generating a tomographic image of the positron annihilation event

DRAWINGS

DESCRIPTION

Figure 1:
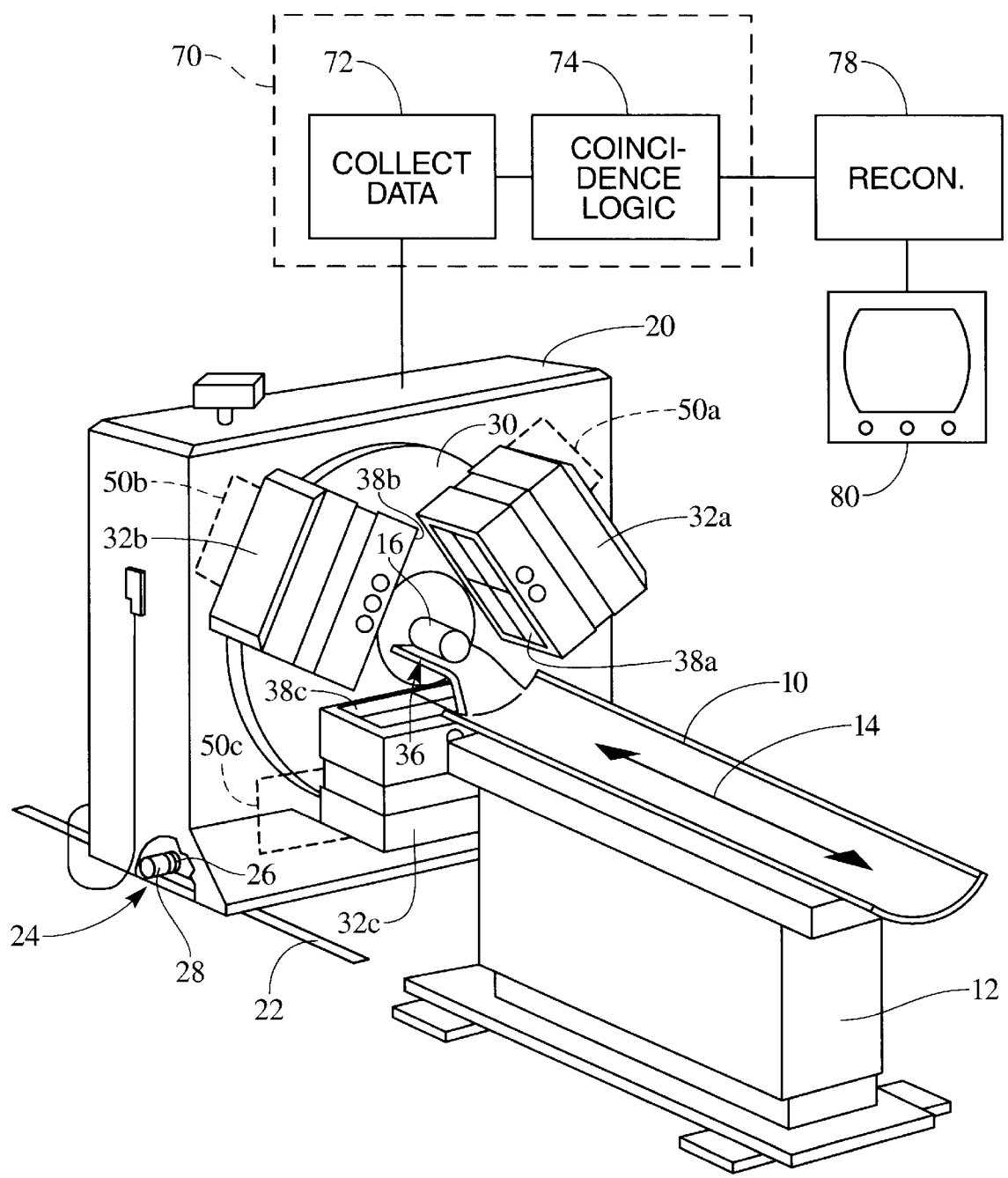
FIG. 1 is a diagrammatic illustration of a gamma camera according to the present invention.

With reference to FIG. 1, a diagnostic imaging system includes a subject support or table which is mounted to stationary, vertical supports 12 at opposite ends. The subject table is selectively positionable up and down to center a subject 16 in the center of a circle along a longitudinal axis 14.

An outer gantry structure 20 is movably mounted on tracks 22 which extend parallel to the longitudinal axis. This enables the outer gantry structure to be moved parallel to the longitudinal axis 14. An outer gantry structure moving assembly 24 is provided for selectively moving the outer gantry structure 20 along the tracks 22 in a path parallel to the longitudinal axis. In the illustrated embodiment, the longitudinal moving assembly includes drive wheels 26 for supporting the outer gantry structure on the tracks. A motive power source, such as a motor 28, selectively drives one of the wheels which frictionally engages the track and drives the outer gantry structure and supported inner gantry structure and detector heads therealong. Alternately, the outer gantry can be stationary and the subject support configured to move the subject along the longitudinal axis.

An inner gantry structure 30 is rotatably mounted on the outer gantry structure 20. A first camera or radiation detector head 32a is mounted to the inner gantry structure. Second and third radiation detector heads 32b, 32c are mounted to the inner gantry structure orthogonal to the first camera head. Of course, the detectors may be positioned to oppose each other at any angle suitable for detecting radiation. It is to be further appreciated that a greater or lesser number of detectors can be provided and detectors having non-planar radiation receiving surfaces can be used. In coincidence imaging, at least two detectors are required.

The detectors 32a, 32b, 32c detect radiation, the type of which depends on the type of imaging performed. In positron coincidence imaging, the radiation comprises 511 keV gamma radiation characteristic of positron annihilation events. The inner gantry structure defines a central, subject receiving examination region 36 for receiving the subject table and, particularly along the longitudinal axis. The examination region 36 is enlarged to receive the detector heads in any of a variety of displacements from a central axis and angular orientations.

The detectors each include a scintillation crystal disposed behind a radiation receiving face 38a, 38b, 38c, respectively, that is viewed by an array of photomultiplier tubes. The scintillation crystal emits a flash of light in response to incident radiation. The array of photomultiplier tubes convert the light into electrical signals. A resolver circuit resolves the x,y coordinates at of each light flash and the energy of the incident radiation. The relative outputs of the photomultiplier tubes are processed and corrected, as is conventional in the art, to generate an output signal indicative of a longitudinal and transverse coordinate on the detector head at which each radiation event is received, and an energy of each event. The radiation sensitive face of each detector may extend, for example, 300 mm in the transverse direction.

With further reference to FIG. 1, a data collection processor 70 is linked to the detectors 32a, 32b, 32c and the motor and drive assemblies 50a, 50b, 50c. The data collection processor collects data 72 and includes coincidence logic circuitry 74 which determines whether gamma radiation is detected by two of the detectors 32a, 32b, 32c substantially simultaneously. More specifically, the coincidence logic 74 determines whether both detectors detect a gamma ray within a predetermined coincidence time interval, for example on the order of 15 nanoseconds. If so, the events are captured as corresponding to a coincidence event. A reconstruction processor 78 processes the data to generate one or more tomographic image slices indicative of the distribution of the radiopharmaceutical within the patient. The images are displayed in human readable form on a display device 80 such as a monitor, film, or the like.

To position the radiation detectors in desired orientations and distances from the subject, a drive assembly 50a, 50b, 50c is associated with each detector assembly 32a, 32b, 32c. Each detector may be moved tangentially with respect to the imaging region as well as radially toward and away from the imaging region. The relative angular orientations of the detectors 32a, 32b, 32c about the imaging region may also be varied. In a preferred embodiment, movement of the radiation detectors is carried out using the apparatus described in co-pending application Ser. No. 08/757,874 now U.S. Pat. No. 5,838,009 filed Nov. 27, 1996 and assigned to the present assignee. Alternately, a single motor and drive assembly controls movement of all detector heads individually or as a unit.

Figure 2:
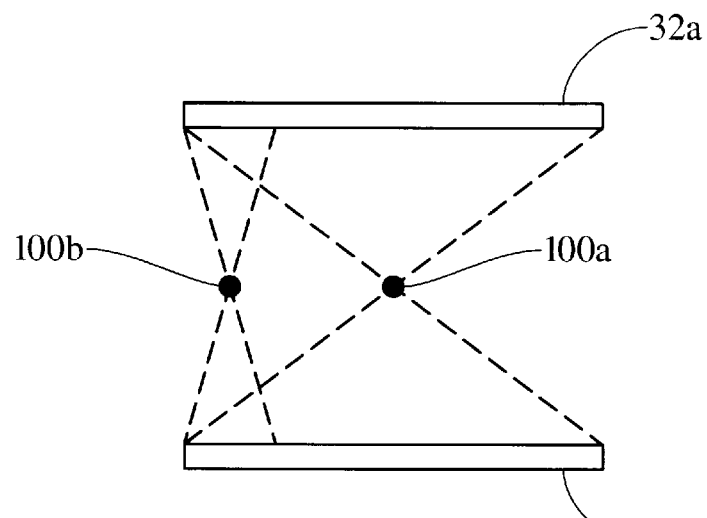
FIG. 2 depicts two detectors in a 180 degree opposed configuration.

With reference to FIG. 2, two detectors 32a, 32b may be positioned in a relative angular orientation in which the detectors face each other across the imaging region, i.e. in a 180 degree opposed configuration. The sensitivity of such a detector configuration peaks at the center of the transverse field of view and falls to zero at the edges. As illustrated by coincidence events 100a, 100b in FIG. 2, this variation occurs because the angle of acceptance for coincidence events depends on the location of an event within the transverse field of view of the detectors.

Figure 3:
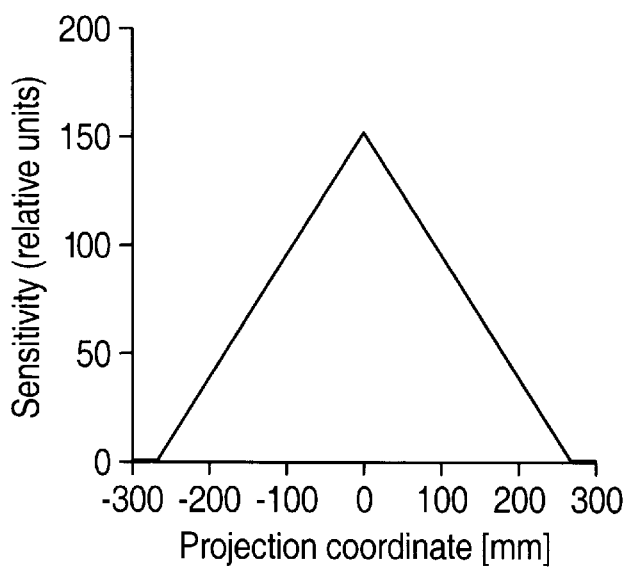
FIG. 3 depicts the sensitivity profile for the configuration depicted in FIG. 3.

In a tomographic acquisition, the inner gantry portion and hence the detectors are rotated about the imaging region. Conventionally, the axis of rotation has coincided with the center of the detectors' transverse field of view. The resultant variation in sensitivity within a slice can be depicted graphically as the sensitivity profile shown in FIG. 3. As the detectors are rotated about the imaging region during a scan, a given line of coincidence intersects both detectors only at certain range of detector angles. The sensitivity to this line of coincidence is proportional to this angular range. As a result, the sensitivity depends on the distance from the center of rotation. As can be seen from FIG. 3, the sensitivity profile is triangular in shape.

This variation in sensitivity can be taken into account by a transverse geometric correction. The projection coordinates are rescaled according to this profile in order to normalize the reconstructed images. Although the geometric correction equalizes the apparent sensitivity across the field of view, it cannot equalize the noise statistics across the field of view. Rescaling the data in a low sensitivity region does not change the fact that few actual counts are acquired there. As a result, the signal-to-noise ratio worsens near the edge of the field of view. The clinically usable field of view is therefore limited by the sensitivity fall off.

Figure 4:
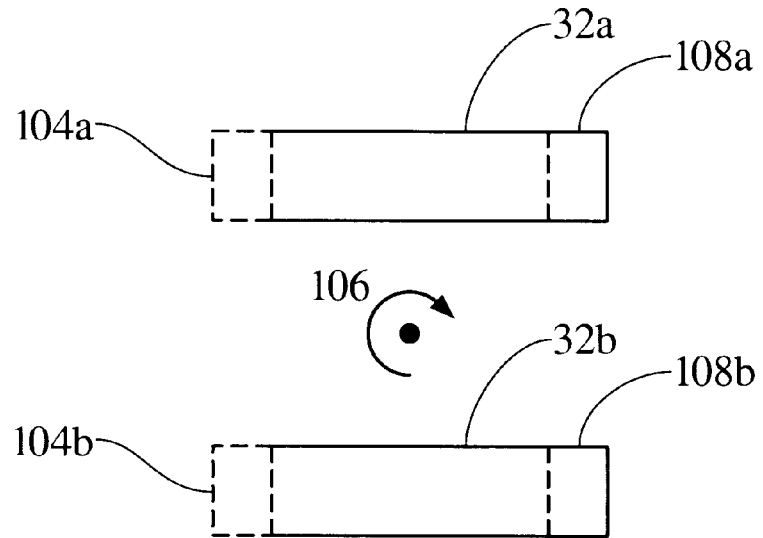
FIG. 4 depicts a detector configuration in which the center of the transverse fields of view is offset from the center of rotation.

With reference to FIG. 4, the sensitivity profile of the detectors 32a, 32b may be made more uniform by moving the them in a transverse direction, i.e. in a direction generally tangential to the imaging region. The dashed lines 104a, 104b depict a symmetric configuration where the center of the transverse field of view of the detectors coincides with the center of rotation 106. Advantageously, the detectors may be positioned so that the centers of their transverse fields of view are offset from the axis of rotation. Such an asymmetric detector configuration is depicted by solid lines 108a, 108b.

Figure 5:
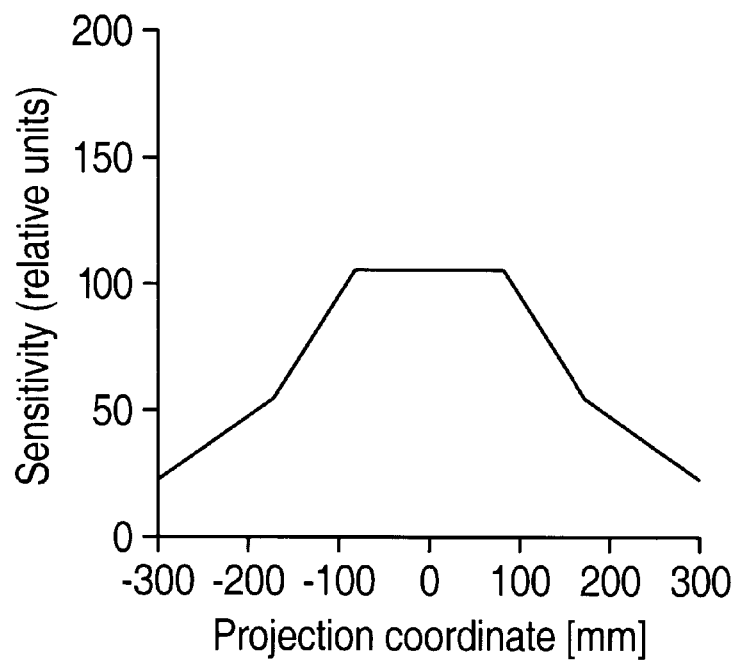
FIG. 5 depicts the sensitivity profile for the configuration depicted in FIG. 4.

The sensitivity profile of a configuration where the center of the transverse fields of view has been offset from the axis of rotation by 10 cm is depicted in FIG. 5. As can be seen, the sensitivity within the circle traced by the centers of the fields of view remains substantially constant. In effect, some of the counts at the center of the field of view have been redistributed to the edge of the field of view, while the total sensitivity (the area under the profile) has remained substantially unchanged. The offset configuration increases the clinically useful field of view, which provides additional flexibility in scanning medium and larger size patients. Alternately, relatively smaller detectors may be used. In addition, the accuracy in positioning the area of interest at the center of rotation is less important.

The overall sensitivity and count rate of a coincidence detection system may be further improved by positioning additional detector heads about the imaging region, thereby improving image quality and reducing scanning time. A triple head coincidence detection system, for example, may be understood as three dual-head coincidence systems where head 1 is in coincidence with head 2, head 2 is in coincidence with head 3, and head 3 is in coincidence with head 1. The sensitivity profile is a function of both the detector configuration and location within the field of view.

Figure 6A:
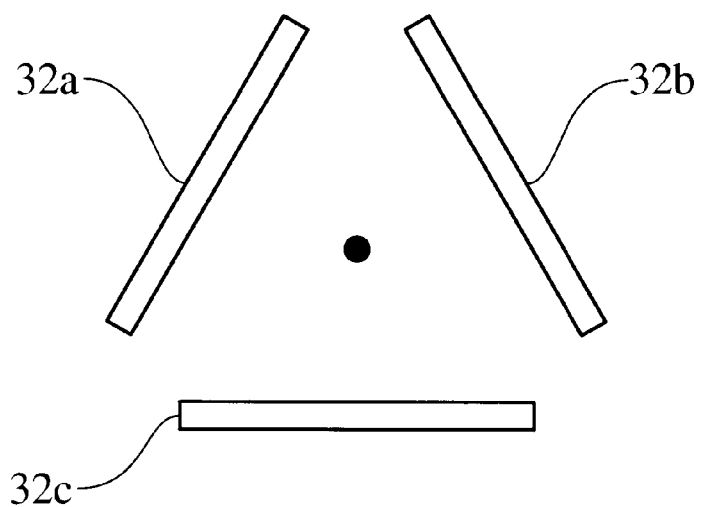
FIGS. 6a and 6b depicts exemplary detector configurations for a gamma camera having three detector assemblies.
Figure 6B:
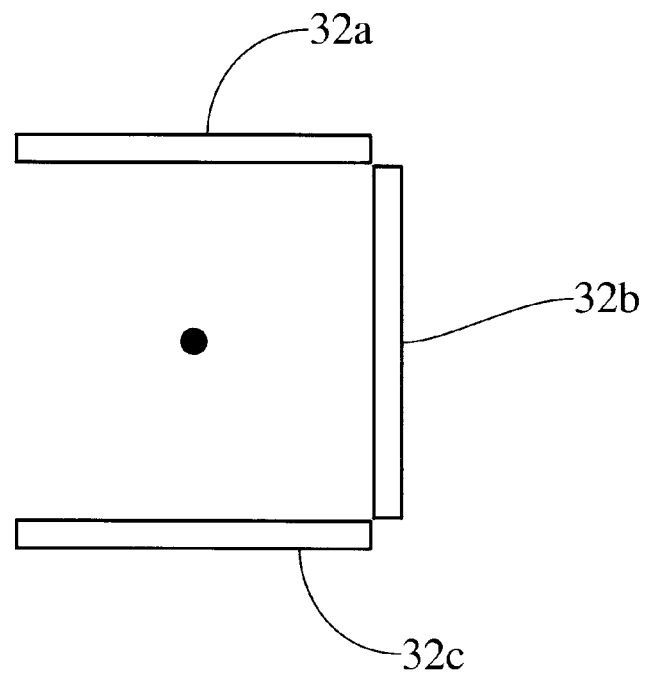
Figure 7A:
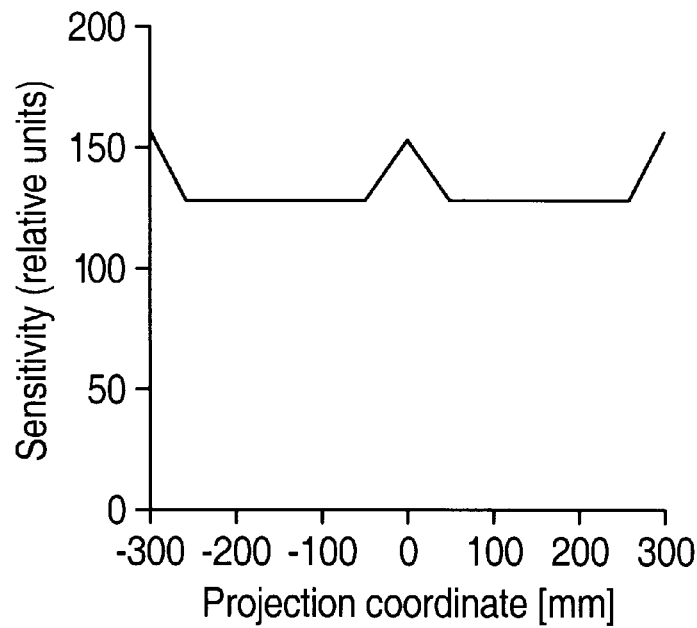
FIGS. 7a and 7b depict the sensitivity profiles for the configurations depicted in FIGS. 6a and 6b.
Figure 7B:
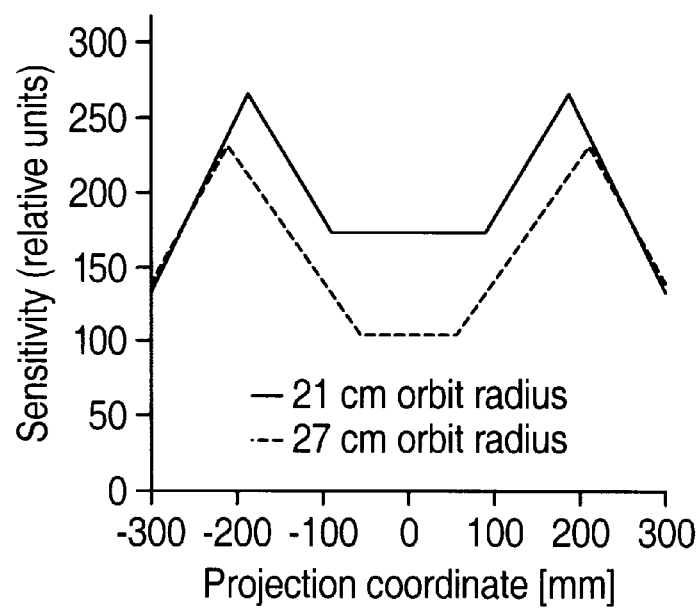

Exemplary detector configurations for a three-head system are depicted in FIGS. 6a and 6b. FIG. 6a depicts a configuration wherein the detectors 32a, 32b, 32c are disposed at equal angular intervals about the imaging region, e.g. at 120 degree angular intervals. FIG. 6b depicts a configuration wherein the detectors 32a, 32b, 32c are positioned at 90 degree angular intervals. Sensitivity profiles for the configurations depicted in FIGS. 6a and 6b are depicted at FIGS. 7a and 7b, respectively. Of course, other detector configurations may also be implemented.

Hence, the configuration of the detectors may be adjusted in order to optimize the sensitivity profile according to the needs of a particular imaging procedure. The 120 degree configuration requires only a 120 degree gantry rotation and, as can be seen from FIG. 7, has a higher overall sensitivity. With particular reference to FIG. 7a, the sensitivity of the 120 degree configuration depends strongly on radial distance between the radiation sensitive face of a detector and the center of rotation, i.e. the orbit radius. This is particularly true near the center of the field of view.

Figure 8:
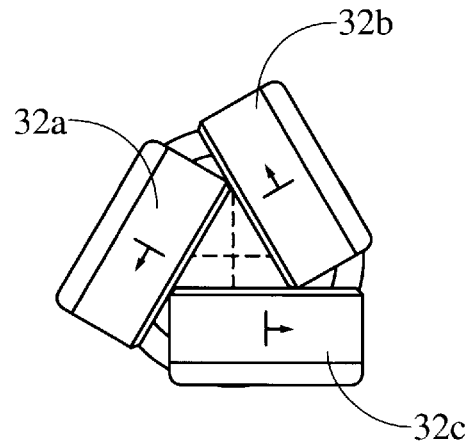
FIG. 8 depict an additional exemplary detector configuration for a gamma camera having three detector assemblies.

However, the minimum permissible orbit radius is influenced by the size of the object or the region of the anatomy being imaged. For example, physical contact between the detectors and the object being imaged is generally undesirable. Hence, relatively larger objects or regions of the anatomy require relatively larger orbit radii, whereas relatively smaller objects or regions of the anatomy permit relatively smaller orbit radii. It should be noted that, in the preferred embodiment, the detectors are movable in tangential and radial directions so that the detectors may be irised as shown in FIG. 8. Thus, minimum orbit radius is not limited by the transverse dimension of the detector assemblies. As with the two detector configuration, the detectors in a three head configuration may also be offset in the tangential direction to allow improved central coverage.

Because a smaller orbit radius provides a higher sensitivity within the center of the field of view, the 120 degree configuration is particularly advantageous for scanning relatively smaller objects or regions of the anatomy. As the object becomes larger, however, the orbit radius must be increased, thereby decreasing sensitivity within the center of the field of view. Thus, the 120 degree configuration is less well suited for imaging relatively larger objects or regions of the anatomy.

The sensitivity of the 120 degree configuration also peaks near the edges of the field of view. Thus, the 120 degree configuration is also well suited for imaging procedures in which the region of interest is offset from the center of the field of view.

The sensitivity profile of a configuration in which the detectors are positioned at 90 degree angular intervals is shown in FIG. 7b. The sensitivity is substantially uniform over a relatively large field of view. As can be seen from a comparison of FIGS. 7a and 7b, the sensitivity within the center of the field of view of the 90 degree configuration is less than that of the 120 degree configurations when the orbit radius of the 120 degree configuration is relatively smaller but greater than that of the 120 degree configuration when the orbit radius is relatively larger. Thus, there is an orbit radius at which the sensitivities are substantially equal.

Above this orbit radius, the 90 degree configuration provides greater sensitivity, especially when the region of interest in the object of interest is near to the center of the field of view. Thus, the 90 degree angular interval configuration may be advantageously employed when imaging relatively large regions of the anatomy, large or obese patients, or where a relatively large orbit radius is otherwise required. Alternately, the 120 degree configuration may advantageously be employed to image smaller objects or regions of the anatomy.

Other detector configurations may also be used to provide other desirable sensitivity profiles. For example, the detectors may be positioned at 102 degree configuration or a 90 degree/120 degree configuration. These configurations have sensitivities in between the 120 and 90 degree angular interval configurations. The present invention is also not limited to use with circular orbits. Thus, the detectors may be moved radially toward and away from patients or objects having other than circular cross sections.

Further the, the heads can be moved tangentially to optimize the sensitivity profiles for a particular type of image procedures or to maximize coincidence counts within a desired region of the field of view. Thus, tangential motion may be used to compensate for regions having poorer sensitivity.

The invention has been described with reference to the preferred embodiment. Obviously, modifications and alterations will occur to others upon reading an understanding the preceding description. It is intended that the invention be construed as including all such modifications and alterations insofar as they come within the scope of the appended claims or the equivalents thereof.

What is claimed is:

1. A method of imaging utilizing an apparatus which includes a two detector assemblies disposed 180 degrees opposite each other wherein each detector assembly includes a radiation sensitive face which faces an imaging region, generates an output signal indicative of the axial and transverse coordinates on the radiation sensitive face at which the radiation has been detected, and has a field of view in the transverse direction, the method comprising:

detecting gamma radiation characteristic of a plurality of positron annihilation events;

rotating the detectors about an axis of rotation, wherein the centers of the transverse field of view of the detectors are offset from the axis of rotation and wherein the centers of the transverse fields of view coincide;

repeating the step of detecting; and generating an image indicative of the positron annihilation events.

2. The method of claim 1 wherein the image is a tomographic image.

3. The method of claim 1 wherein each detector assembly includes a plurality of radiation sensitive elements disposed in a two dimensional array.

4. The method of claim 3 wherein the radiation sensitive elements are photomultiplier tubes.

5. A method of imaging utilizing an apparatus which includes a plurality of detector assemblies wherein each detector assembly includes a radiation sensitive face which faces an imaging region, generates an output signal indicative of the axial and transverse coordinates on the radiation sensitive face at which the radiation has been detected, and has a field of view in the transverse direction, the method comprising:

detecting gamma radiation characteristic of a plurality of positron annihilation events;

moving the detectors in a tangential direction until the offset between the centers of the transverse fields of view of the detectors and the axis of rotation reaches a desired value;

rotating the detectors about an axis of rotation, the centers of the transverse field of view of the detectors being offset from the axis of rotation;

repeating the step of detecting; and generating an image indicative of the positron annihilation events.

6. The method of claim 5 wherein the apparatus includes three detector assemblies and further including the steps of:

determining an orbit radius required to image an object located in the imaging region; and depending on the required orbit radius, determining a desired relative angular orientation of the detector assemblies; and positioning the detector assemblies in the desired relative angular orientation.

7. The method of claim 6 comprising the step of positioning the detector assemblies at 120 degree angular intervals if the required orbit radius is less than a threshold value.

8. A method of imaging utilizing an apparatus which includes a plurality of radiation detectors disposed about an examination region, the method comprising:

determining an orbit radius to be used in an imaging procedure;

depending on the orbit radius, adjusting the relative angular orientation of the radiation detectors;

detecting gamma radiation characteristic of a plurality of positron annihilation events;

rotating the radiation detectors with respect to the examination region;

repeating the steps of detecting and rotating; and generating a tomographic image indicative of the positron annihilation events.

9. The method of claim 8 wherein the step of adjusting includes positioning the detectors at equal angular intervals with respect to the imaging region.

10. The method of claim 9 wherein the apparatus has three radiation detectors.

11. The method of claim 8 wherein the radiation detectors comprise a plurality of radiation sensitive elements disposed in a two dimensional array.

12. The method of claim 11 wherein the array is planar.

* * * * *